United States Patent [19]

Wallace

[11] 4,341,520
[45] Jul. 27, 1982

[54] DENTAL HANDPIECE BEARING SUSPENSION SYSTEM

[76] Inventor: Richard A. Wallace, 2750 Audubon Rd., Audubon, Pa. 19407

[21] Appl. No.: 226,408

[22] Filed: Jan. 19, 1981

[51] Int. Cl.³ .............................................. A61C 1/05
[52] U.S. Cl. .................................................. 433/132
[58] Field of Search ....................... 433/133, 131, 132; 428/809

[56] References Cited

U.S. PATENT DOCUMENTS 3,218,028 11/1965 Borden ................................ 433/132

Primary Examiner—Robert Peshock
Attorney, Agent, or Firm—Rene A. Kuypers

[57] ABSTRACT

A dental handpiece is disclosed for rotating a bur in a housing having an enclosing cap, utilizing an air-driven, axial-flow turbine mounted on a shaft between two ball bearings, the assembly forming a removeable cartridge. Air is directed to the turbine through a combination plenum and nozzle ring. The cartridge is acoustically isolated from the cap and housing by two elastomeric rings having separate radial segments and axial pads. The radial segments support the cartridge bearings, prevent outer race rotation, compensate for dimensional variation of the elastomeric rings and cap and housing bores, and provide a means to vary suspension stiffness. The axial pads of the elastomeric ring around the front bearing provide a bearing pre-load force independent of the radial forces exerted on the bearing. The axial pads of the elastomeric ring around the rear bearing prevent air leakage from the plenum, seat the nozzle ring securely in the housing, and compensate for dimensional variation of the nozzle ring, housing, and cap, independent of the radial forces on the bearing.

3 Claims, 6 Drawing Figures

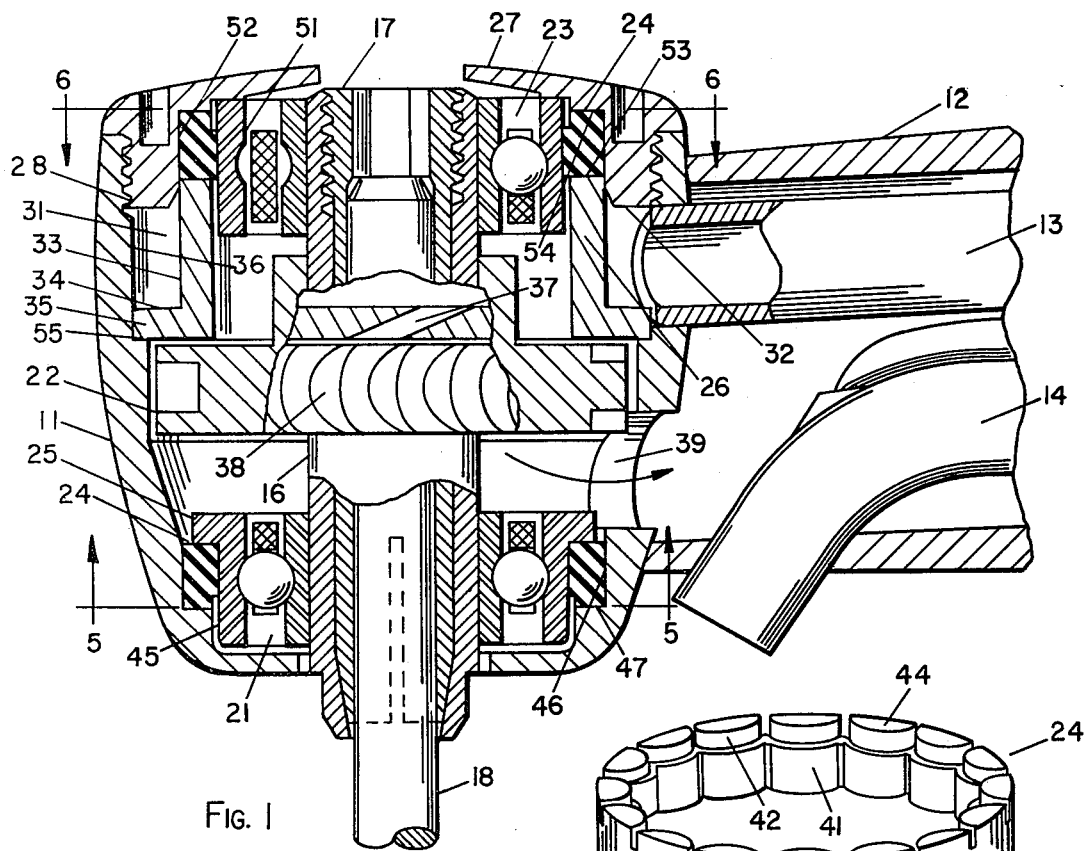
FIG. 1
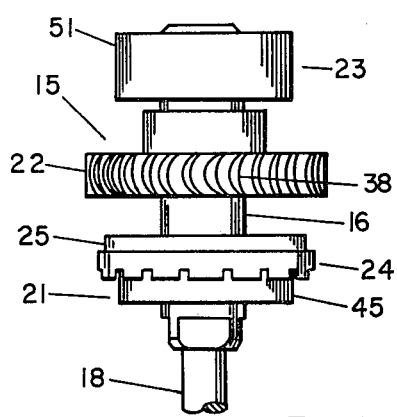
FIG. 2
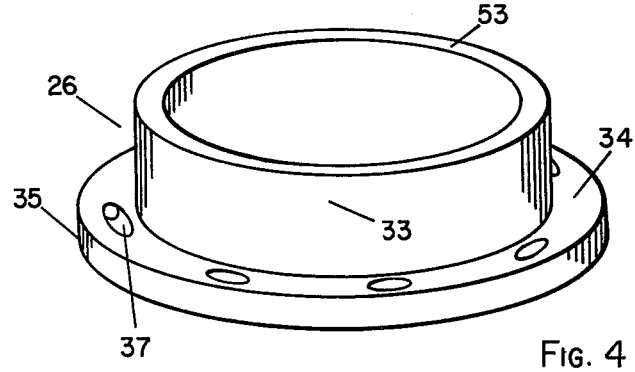
FIG. 3
FIG. 4
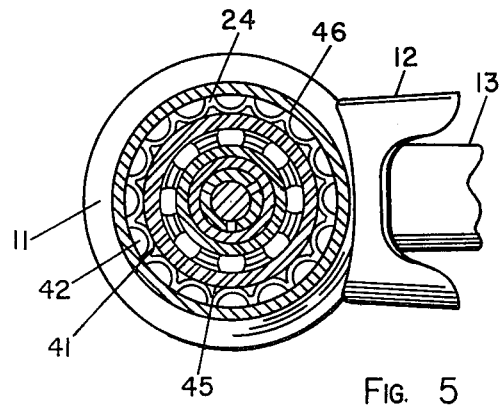
FIG. 5
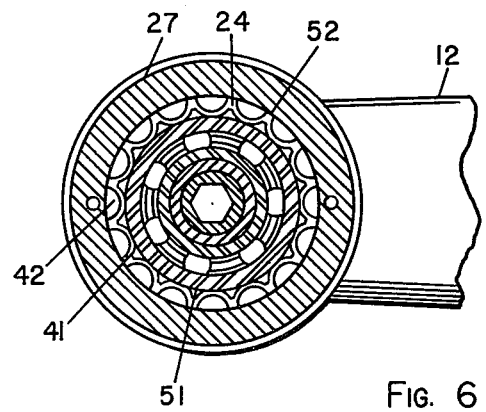
FIG. 6

DENTAL HANDPIECE BEARING SUSPENSION SYSTEM

FIELD OF THE INVENTION

This invention relates to the field of high speed dental handpieces, and in particular to the field of dental handpieces which utilize an axial-flow turbine, and resilient, elastomeric rings to reduce noise, by isolating the rotating parts from the handpiece housing.

BACKGROUND OF THE INVENTION

When belt drives were replaced by air-driven turbines for rotating dental burs, the very high speed of the turbines permitted drilling and other dental operations to be done much faster and with less trauma to the patient than in prior times. The high speed of the rotating parts however, caused several problems not associated with the belt-drive technology. Foremost among the problems were excessive noise, adequate bearing support, and a need for a controlled axial load to prolong bearing life.

Early in the development of turbine driven handpieces a removable cartridge consisting of rotating parts and bearings, and sometimes an enclosing cylinder, was used in the head of the handpiece. An example of a cartridge having a tangential flow turbine is shown in U.S. Pat. No. 3,074,167, while a cartridge with an axial flow turbine in it is shown in U.S. Pat. No. 3,411,210. In these patents, the cartridges were mounted directly in the handpiece housings without any accoustical isolation. The handpieces were quite noisy, and very precise machining of the housing bores was required to prevent outer race rotation of the ball bearings, yet not hold the outer races too tightly.

Noise reduction by isolating the cartridge from the housing through elastomeric rings has been achieved in several ways. In U.S. Pat. No. 3,218,028 one version of the cartridge uses two resilient bushings, while a second version uses two O-rings. Four O-rings are used in U.S. Pat. No. 3,268,205. While O-rings reduce noise and provide bearing support, they do not provide sealing or axial bearing pre-loading.

Formed noise-reducing collar members are shown in U.S. Pat. No. 3,134,172, while vibration absorbers having similar cylindrical and flanged elements are shown in U.S. Pat. No. 3,376,084. While the flanged sections of these rings form an axial loading means, the solid, thin flanges have a very high spring rate, making reliable control of the axial force very difficult to achieve.

SUMMARY OF THE INVENTION

The present invention provides a high-speed dental handpiece having an easily replaceable cartridge consisting of a front flanged and a rear cylindrical ball bearing, an air-driven, axial flow turbine, a shaft, and a collet. The cartridge holds a bur, rotates in a stepped housing bore, and is accessible through a removeable cap. Air is directed to the turbine blades through a nozzle ring which in conjunction with the interior surfaces of the housing bore and cap, form an air plenum.

The primary object of this invention is to provide the cartridge with a simple suspension means which performs a variety of functions, including reducing noise, preventing outer bearing race rotation, varying radial stiffness, compensating for dimensional variation of parts, sealing air leakage, and producing a controlled bearing pre-load force.

Surrounding each bearing is an elastomeric ring having a plurality of equal, arcuate, interior segments. Located upon each of the segments are arcuate, interior pads which are integrally formed with and smaller than the segments. The exterior surface of the ring is smooth and circular, and the remaining surfaces are flat.

The segments of the elastomeric ring around the front flanged bearing isolate it from the housing to reduce noise, and compensate for dimensional variations of the ring and the housing bore. They also provide a squeezing force which prevents rotation of the outer bearing race, and a means whereby the radial mounting stiffness can be varied by changing the housing bore dimension. In addition, the pads of the ring pressing against the bearing flange provide an axial load on the cartridge bearings, independent of the radial squeeze load on the front bearing.

The segments of the elastomeric ring around the rear cylindrical bearing isolate it from the cap to reduce noise, and compensate for dimensional variations of the ring and the cap bore. They also provide a squeezing force which prevents rotation of the outer bearing race, and a means whereby the radial mounting stiffness can be varied by changing the cap bore dimension. In addition, the pads of the ring provide an axial force to seat the nozzle ring securely in the stepped housing bore, prevent air leakage from the plenum, and compensate for dimensional variations of the nozzle ring, the housing, and the cap, independent of the radial squeeze load on the rear bearing.

BRIEF DESCRIPTION OF THE DRAWINGS

FIG. 1 is a sectional elevational view of the handpiece head and its supporting handle.

FIG. 2 is an elevational view of the cartridge and the front elastomeric ring.

FIG. 3 is a perspective view of the rear elastomeric ring.

FIG. 4 is a perspective view of the nozzle ring.

FIG. 5 is a sectional view of the head along the lines 5—5 of FIG. 1, looking in the direction of the arrows.

FIG. 6 is a sectional view of the head along the lines 6—6 of FIG. 1, looking in the direction of the arrows.

DETAILED DESCRIPTION OF THE INVENTION

The high speed dental handpiece of this invention as shown in FIG. 1 consists of a housing 11 which is attached to a hollow handle 12, only partially shown. The hollow handle 12 encloses a tube 13 for transmitting air to the housing 11, and a curved tube 14 which provides the services of water, chip air, and light required by the handpiece. The curved tube 14 and the services provided by it are disclosed in detail in my co-pending patent application, Ser. No. 06/105,595, filed Dec. 20, 1979.

Located within the housing 11 is a cartridge 15 which is shown in detail in FIG. 2. The cartridge 15 consists of a shaft 16 holding a collet 17 (FIG. 1) which in turn firmly grips a bur 18. Attached to shaft 16 is a front flanged ball bearing 21, an axial flow turbine 22, and a rear ball bearing 23. Elastomeric ring 24 is located upon front ball bearing 21 and rests against flange 25.

Referring again to FIG. 1, the cartridge 15 is shown positioned in the center of housing 11. Surrounding rear bearing 23 is a nozzle ring 26 and a second elastomeric ring 24. When cap 27 is threaded into housing 11 through threads 28, the cartridge 15 is securely supported within housing 11, and elastomeric ring 24 located around front bearing 21 causes a pre-load upon bearings 21, 23.

Air from supply tube 13 enters a circular plenum 31. The cross section of plenum 31 is defined by four surfaces comprising the cap bottom 32, the outer cylindrical surface 33 of nozzle ring 26 (shown in perspective in FIG. 4), the flat surface 34 of nozzle ring flange 35, and the major bore 36 of housing 11. In operation, air is supplied through tube 13 to plenum 31 where it exits through angled holes 37 in flange 35. After exiting from holes 37, the air impinges on arcuate shaped blades 38 of turbine 22 and exits housing 11 along the directiion of the arrow through port 39 into the hollow interior of handle 12.

Referring now to FIG. 3, the elastomeric ring 24 is composed of arcuate, interior segments 41. Located upon each of the segments 41 are arcuate, interior pads 42 which are integrally formed with and smaller than the segments 41. The exterior surface 43 of ring 24 is smooth and circular, and the remaining surfaces 44 are flat.

The segments 41 of the elastomeric ring 24 around the front flanged bearing 21 isolate it from the housing 11 to reduce noise. As shown in FIG. 5, segments 41 are compressed by the front bearing's outer race 45. The compression of the segments 41 compensate for variations in the dimensions of ring 24 and the minor housing bore 46. Segments 41 also provide a squeezing force which prevents rotation of outer bearing race 45, and additionally provide a means whereby the radial mounting stiffness of cartridge 15 (FIG. 2) can be varied by changing the dimension of housing bore 46.

The pads 42 of the elastomeric ring 24 by pressing against flange 25 of front bearing 21 and the housing step 47 (FIG. 1) provide an axial pre-load on bearings 21 and 23 independent of the radial squeeze load caused by segments 41 on front bearing outer race 45.

The segments 41 of the elastomeric ring 24 around the rear bearing 23 isolate it from the cap 27 to reduce noise. As shown in FIG. 6, segments 41 are compressed by the rear bearing's outer race 51. The compression of the segments 41 compensate for variations in the dimensions of ring 24 and the cap bore 52. Segments 41 also provide a squeezing force which prevents a rotation of outer bearing race 51, and additionally provide a means whereby the radial mounting stiffness of cartridge 15 (FIG. 2) can be varied by changing the dimension of cap bore 52.

The pads 42 of the elastomeric ring 24 by pressing against the top surface 53 (FIG. 1) of nozzle ring 26 and the flat inner surface 54 of cap 27 provide an axial force to seat the nozzle ring 26 securely upon the housing bore step 55, prevent air leakage from plenum 31, and compensate for dimensional variations in nozzle ring 26, housing 11, and cap 27, independent of the radial squeeze load caused by segments 41 on rear bearing outer race 51.

What is claimed is:

1. In a dental handpiece for rotating a bur in a housing, having a turbine mounted on a shaft between a front and rear ball bearing, said front bearing having an inner race and a flanged outer race, the improvement comprising:
    an elastomeric ring comprising a plurality of equal segments each having an interior arcuate surface, an exterior surface which is smooth and circular, a plurality of discrete, arcuate pads positioned upon said arcuate segments wherein a single pad is integrally formed with and smaller than a single arcuate segment, the remaining surfaces being flat,
    said elastomeric ring positioned around the front ball bearing outer race, and being held in place radially by the cylindrical section of the outer race, and axially by the flange,
    whereby the segments of the elastomeric ring provide compensation for dimensional variations of the ring and housing bore, and provide a squeezing force to lessen noise and prevent outer race rotation of the front bearing, and further,
    whereby the pads of said elastomeric ring provide an axial pre-load on said bearing, independent of the radial squeeze load.

2. In a dental handpiece for rotating a bur in a housing, having a rear cap and a stepped bore, and including an axial flow turbine powered by air jets from a nozzle ring, wherein said turbine is mounted on a shaft between a front and a rear ball bearing, said rear ball bearing having an inner race and a cylindrical outer race, the improvement comprising:
    an elastomeric ring comprising a plurality of equal segments each having an interior arcuate surface, an exterior surface which is smooth and circular, a plurality of discrete, arcuate pads positioned upon said arcuate segments wherein a single pad is integrally formed with and smaller than a single arcuate segment, the remaining surfaces being flat,
    said elastomeric ring positioned around the rear ball bearing outer race, and being held in place by the nozzle ring and an inner surface of the cap,
    whereby the segments of the elastomeric ring provide compensation for dimensional variations of the ring and cap bore, and provide a squeezing force to lessen noise and prevent outer race rotation of the rear bearing, and further,
    whereby the pads of said elastomeric ring provide an axial force to seat said nozzle ring securely in the stepped housing bore and prevent air leakage, independent of the radial squeeze load on the bearing.

3. In a dental handpiece in accordance with claim 2 wherein:
    a second elastomeric ring is positioned around the front ball bearing outer race, and is held in place radially by the cylindrical section of the outer race and the housing bore, and axially by the bearing flange and the housing bore step,
    whereby the segments of the elastomeric ring provide compensation for dimensional variation of the ring and housing bore, and provide a squeezing force to lessen noise and prevent outer race rotation of the front bearing, and further,
    whereby the pads of said elastomeric ring provide an axial spring pre-load on said bearings, independent of the radial squeeze load on said front bearing.

* * * * *